(12) United States Patent
Chen et al.

(10) Patent No.: US 11,844,948 B2
(45) Date of Patent: Dec. 19, 2023

(54) MULTI-SENSOR COMPOSITE RIGHT VENTRICULAR ELECTRODE AND FUSED CARDIAC RATE ADAPTIVE PACING METHOD

(71) Applicant: XI'AN JIAOTONG UNIVERSITY, Xi'an (CN)

(72) Inventors: Xiang Chen, Xi'an (CN); Jin Li, Xi'an (CN); Zhongbo Bai, Xi'an (CN); Hua Jin, Xi'an (CN); Quangui Qu, Xi'an (CN); Fenghu Zhou, Xi'an (CN); Feng Yun, Xi'an (CN); Ke Han, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 497 days.

(21) Appl. No.: 17/040,044

(22) PCT Filed: Dec. 26, 2018

(86) PCT No.: PCT/CN2018/124054
§ 371 (c)(1),
(2) Date: Sep. 21, 2020

(87) PCT Pub. No.: WO2019/196504
PCT Pub. Date: Oct. 17, 2019

(65) Prior Publication Data
US 2021/0016095 A1    Jan. 21, 2021

(30) Foreign Application Priority Data
Apr. 8, 2018    (CN) .......................... 201810307892.8

(51) Int. Cl.
*A61N 1/36*    (2006.01)
*A61N 1/365*   (2006.01)

(52) U.S. Cl.
CPC ....... *A61N 1/36585* (2013.01); *A61N 1/3655* (2013.01); *A61N 1/36521* (2013.01)

(58) Field of Classification Search
CPC ............ A61N 1/36585; A61N 1/36521; A61N 1/3655; A61N 1/056; A61N 1/36514;
(Continued)

(56) References Cited

U.S. PATENT DOCUMENTS

| 6,714,823 B1 * | 3/2004 | De Lurgio | ............. | A61N 1/056 |
| | | | | 600/585 |
| 8,092,386 B1 * | 1/2012 | Wenzel | ............. | A61M 5/14276 |
| | | | | 600/323 |

(Continued)

FOREIGN PATENT DOCUMENTS

| CN | 102526879 A | 7/2012 |
| CN | 105120944 A | 12/2015 |

(Continued)

OTHER PUBLICATIONS

Seifert, G.P. et al. "In Vivo and In Vitro Studies of a Chronic Oxygen Saturation Sensor." Oct. 31, 1991.

(Continued)

*Primary Examiner* — Rex R Holmes
(74) *Attorney, Agent, or Firm* — W&G Law Group

(57) ABSTRACT

Provided is an accurate, fast and long-term stable fused CRAP. The electrode includes a positioning anchor, a silicone catheter, a sensor compartment and a connecting wire. The method monitors physiological information such as blood PPG, blood oxygen saturation, temperature and impedance of blood in the right ventricular cavity, and monitors blood temperature information, which is also a slowly changing metabolic rate, to provide cross-comparison with blood oxygen saturation information, improving monitoring accuracy of blood oxygen saturation. The rap- (Continued)

idly changing right ventricular apical impedance information is monitored to improve rapid response ability of CRAP. The LEDs driving current is dynamically adjusted by monitoring the internal temperature of the PPG sensor and the impedance change of the attached biological tissue, which indirectly reflects thickness change of the attached biological tissue, thereby delaying the failure time of the PPG sensor.

3 Claims, 5 Drawing Sheets

(58) Field of Classification Search
CPC .............. A61N 1/36557; A61N 1/3702; A61N 1/3704; A61B 5/01; A61B 5/0538; A61B 5/14551; A61B 5/1459; A61B 5/4836; A61B 2562/166; A61B 5/6852; A61B 5/053; A61B 5/14552; A61B 5/02055
See application file for complete search history.

(56) References Cited

U.S. PATENT DOCUMENTS

| | | |
|---|---|---|
| 2011/0152963 A1 | 6/2011 | Stahmann et al. |
| 2012/0316416 A1* | 12/2012 | Spear .................... A61N 1/056 600/374 |
| 2016/0338629 A1 | 11/2016 | Doerr |
| 2016/0361021 A1* | 12/2016 | Salehizadeh ....... A61B 5/02416 |
| 2017/0049336 A1* | 2/2017 | Hatch ................ A61B 5/02427 |

FOREIGN PATENT DOCUMENTS

| | | |
|---|---|---|
| CN | 106456003 A | 2/2017 |
| CN | 106730350 A | 5/2017 |
| CN | 206745746 U | 12/2017 |
| CN | 108577816 A | 9/2018 |

OTHER PUBLICATIONS

International Search Report (PCT/CN2018/124054); dated Apr. 1, 2019.

* cited by examiner

MULTI-SENSOR COMPOSITE RIGHT VENTRICULAR ELECTRODE AND FUSED CARDIAC RATE ADAPTIVE PACING METHOD

CROSS-REFERENCE TO RELATED APPLICATIONS

This application is a continuation of International Application No. PCT/CN2018/124054, filed on Dec. 26, 2018, which claims priority to Chinese Patent Application No. 201810307892.8, filed on Apr. 8, 2018. The disclosures of the aforementioned applications are hereby incorporated by reference in their entireties.

TECHNICAL FIELD

The present application belongs to the field of biomedical engineering, and relates to a multi-sensor composite right ventricular electrode and a fused cardiac rate adaptive pacing (CRAP) method.

BACKGROUND

More than 50% of cardiac pacemaker-implanted subjects lost their autonomous cardiac rhythm due to sick sinus syndrome, and more than 90% of these subjects chose to implant a CRAP pacemaker. In China, although CRAP pacemakers implanted each year take more than 50% of the total pacemaker implants, most of the CRAP rely on non-closed loop controlled motion sensors. These sensors are sensitive to motions, but are not sensitive to changes in non-motion metabolisms such as mood and mental activities. In some special cases, for example, when an implanted subject goes down the stairs, the subject will have faster heart rate than when she or he goes up the stairs, thereby causing discomfort of the subject. By adjusting the heart rate with the closed-loop controlled metabolic sensors, the above problems can be solved, so as to provide a heart rhythm adjustment similar to those in physiological conditions during sports, emotions and mental activities.

In the prior art, electrodes for measuring the blood oxygen saturation of mixed veins or central veins, when placed in the right ventricular cavity, can be used to sense the metabolism to perform the closed-loop control for adjusting the heart rhythm. These electrodes usually detect the blood oxygen saturation of the right ventricle blood with a photoplethysmography (PPG) sensor, which is arranged close to the head. A drop of the blood oxygen saturation indicates that the body's oxygen consumption increases due to exercise or other factors, and thus the pacemaker connected to the electrode will speed up the pacing rhythm and increases cardiac output to allow more blood to flow through the lung and to provide more oxygen to the body. "An Active Optical Sensor or Monitoring Mixed Venous Oxygen-Saturation for an Implantable Rate-Regulating Pacing System" reports a right ventricular electrode for measuring mixed venous blood oxygen saturation with a 660 nm single-wavelength reflective PPG sensor, in which oxygen absorption information can be acquired by calculating the product of a cardiac output volume and the arterial-venous blood oxygen saturation difference, thereby triggering an acquisition of blood oxygen saturation each beat via a QRS complex wave and performing CRAP. "Long-Term Clinical Performance of a Central Venous Oxygen Saturation Sensor for Rate Adaptive Cardiac Pacing" reports a right ventricular electrode for measuring central venous blood oxygen saturation with a red-infrared light dual-wavelength reflective PPG sensor, in which a ratio of an intensity of the reflected red light and infrared light is measured, a central vein oxygen saturation is acquired by calculating a linear function from the empirical equation, and the CRAP is performed.

The venous blood oxygen saturation-based CRAP, represented by the above methods, usually triggers the acquisition of the right ventricular blood oxygen saturation of each heart beat with QRS complex wave, and reflects systemic metabolic activity information by the absorption and consumption of oxygen in the blood. However, in addition to the influence of metabolism, the venous blood oxygen saturation may also be changed due to other uncertain factors such as changes of oxygen consumption in muscles and other tissues, changes of cardiac output due to fluctuations in gas exchange between blood and tissues, changes of hemoglobin concentration in blood, and changes of arterial blood oxygen saturation, and these uncertain factors results in difficulties of the measurement of the venous blood oxygen saturation. Meanwhile, as the represents of systemic metabolism, the blood oxygen saturation is a physiological measure having a slow response speed. A delay from an exercise event to the drop of the central vein blood oxygen saturation is about 5 seconds, the time constant of the blood oxygen saturation is about 40 seconds, and the response time is about 72 seconds. Therefore, for rapid changes caused by intense exercises, it is difficult for the blood oxygen saturation of the right ventricle blood to make a rapid regulatory response. In addition, the fibrous tissue wrapped around the electrode gradually thickens with the implantation time, which may eventually obscure the optical window and invalidate the PPG sensor.

SUMMARY

In view of the above problems in the prior art, the present invention provides a multi-sensor composite right ventricular electrode and a fused CRAP. A head of the electrode is simultaneously equipped with a PPG sensor, a temperature sensor and an impedance sensor to obtain and cross-compare information such as blood oxygen saturation, temperature and impedance of the blood, and the information, so as to provide an accurate, fast and long-term stable CRAP sensing electrode and a fused heart CRAP.

The present application provides the following technical solutions.

A multi-sensor composite right ventricular electrode comprises a silicone catheter, a positioning anchor disposed outside one end of the silicone catheter, a sensor compartment disposed in the silicone catheter, and a connecting wire connected to the sensor compartment.

The sensor compartment comprises a print circuit board (PCB), as well as a blood oxygen saturation sensor, a temperature sensor and an impedance sensor that are provided on the PCB. The PCB is connected to one end of the connecting wire via an interface.

Preferably, the blood oxygen saturation sensor is a dual-wavelength PPG sensor comprising a red LED configured to emit red light, an infrared LED configured to emit infrared light and a photodiode configured to detect reflected red light and/or infrared light, wherein the red LED, the infrared LED and the photodiode are located on a PCB; the temperature sensor is composed of a thermistor provided on the PCB; and the impedance sensor comprises a pair of titanium metal electrodes arranged on the two ends of the PCB and configured to form an impedance measurement loop with a biological tissue to be measured, and the titanium metal electrodes are ring-shaped and are embedded on the silicone catheter.

Preferably, the red LED and the infrared LED are connected in parallel or in series to form a unit, and in the unit, the thermistor and the photodiode are sequentially arranged between the pair of titanium metal electrodes.

Preferably, the thermistor is configured to: sense a temperature of blood outside the silicone catheter when neither the red LED nor the infrared LED emits light; sense operating temperatures of the red LED and the infrared LED when both the red LED and the infrared LED emit light in a time division manner; and prevent light emitted by the LEDs from directly entering the photodiode without being reflected by the blood.

Preferably, the red LED adopts SML-LX0603 from LUMEX and configured to emit 660 nm red light; the infrared LED adopts SFH4043 from OSRAM and configured to emit 940 nm infrared light; the photodiode adopts NJL6401 from JRC, and the thermistor adopts NCP15XH103F03RC from MURATA.

Preferably, venous blood oxygen saturation is detected by a dual-wavelength PPG sensor with 660 nm red light and 940 nm infrared light, and is described with an equation (1) or (2):

$$S_pO_2 = \alpha - \beta R \quad (1)$$

$$S_pO_2 = \alpha - \beta R - \gamma R^2 \quad (2)$$

where $I_{AC}^{660}$ and $I_{AC}^{940}$ respectively represent alternating-current components of intensities of the red light and infrared light that are reflected by the blood and are measured by the photodiode; $I_{DC}^{660}$ and $I_{DC}^{940}$ respectively represent direct-current components of the intensities of the red light and infrared light that are reflected by the blood;

$$R = \frac{I_{AC}^{660}/I_{DC}^{660}}{I_{AC}^{940}/I_{DC}^{940}};$$

and $\alpha$, $\beta$ and $\gamma$ are all empirical values determined by calibration.

The equation (1) is a first-order linear relationship between the blood oxygen saturation and R. While the venous blood oxygen saturation does not satisfying the first-order linear relationship, is can described with a second-order equation (2).

A fused CRAP using a multi-sensor composite right ventricular electrode, the method comprises.

Step 1: obtaining a right ventricular blood temperature, a right ventricular blood oxygen saturation, and a right ventricular apical impedance respectively with a temperature sensor, a blood oxygen saturation sensor, and an impedance sensor;

Step 2: generating correspondingly adjusted heart rates on basis of the right ventricular blood temperature-based-CRAP, the right ventricular blood oxygen saturation-based CRAP, and the right ventricular apical impedance-based CRAP, respectively.

Step 3: generating the metabolism-based CRAP through a cross-comparison between the right ventricular blood temperature-based CRAP and the right ventricular blood oxygen saturation-based CRAP; and generating the autonomic nerve system-based CRAP through the right ventricular apical impedance-based CRAP.

Step 4: generating the fused heart CRAP method through a cross-comparison between the metabolism-based CRAP and the autonomic nerve system-based CRAP.

Further, in step 3, said generating the metabolism-based CRAP through the cross-comparison between the right ventricular blood temperature-based CRAP and the right ventricular blood oxygen saturation-based CRAP is represented by the following equation:

$$P_{Meta} = \begin{cases} k_1 P_{Temp} + k_2 P_{S_pO_2} & (P_{Temp} \leq P_{S_pO_2}) \\ P_{Temp} & (P_{Temp} > P_{S_pO_2}) \end{cases},$$

where $P_{Meta}$ is the metabolism-based CRAP obtained through cross-comparison, $P_{Temp}$ is the right ventricular blood temperature-based CRAP, $P_{S_pO_2}$ is the right ventricular blood oxygen saturation-based CRAP, and $k_1$ and $k_2$ are weight coefficients obtained through experiments.

Further, in step 4, said generating the fused CRAP through the cross-comparison between the metabolism-based CRAP and the autonomic nerve system-based CRAP is represented by the following equation:

$$P_{Blend} = \begin{cases} k_3 P_{Meta} + k_4 P_{Imp} & (P_{Meta} \leq P_{Imp}) \\ P_{Meta} & (P_{Meta} > P_{Imp}) \end{cases},$$

where $P_{Blend}$ represents the fused CRAP method obtained through the cross-comparison; $P_{Imp}$ represents the right ventricular apical impedance-based CRAP; and $k_3$ and $k_4$ are weight coefficients obtained through experiments.

Further, a LED driving current is dynamically adjusted by monitoring a change of impedance of a biological tissue attached to a surface of the blood oxygen saturation sensor, the change of impedance indirectly reflecting a change of a thickness of the attached biological tissue.

The change of the thickness of the biological tissue attached to the surface of the blood oxygen saturation sensor is obtained through the following equation:

$$\Delta H = R_0 \left( \sqrt{\frac{k_5}{k_5 - \Delta I_m}} - 1 \right),$$

where $\Delta I_m$ represents the monitored change of impedance of a biological tissue attached to a surface of a PPG sensor; $R_0$ represents a radius of an outer surface of the PPG sensor; $\Delta H$ represents the change of the thickness of the biological tissue attached to the surface of the blood oxygen saturation sensor; $k_5$ is a proportional coefficient obtained by experiments. It is related to a resistivity of the biological tissue, the radius of the outer surface of the PPG sensor, and a distance between measuring electrodes.

The LED driving current is increased in such a manner that, as reflected in the following equation, when the thickness of the attached biological tissue is increased by $\Delta H$, the driving current $C_{D0}$ is increased by $e^{k_6 \Delta H}$ times, $$C_{D0} = C_D e^{k_6 \Delta H},$$

where $C_D$ is a driving current when generating an intensity I of light transmitted through the biological tissue; $C_{D0}$ is a driving current when generating an emission intensity $I_0$ of an LED; and $k_6$ is the product of a light absorption coefficient of the biological tissue and a concentration of a light absorption substance.

When the LED driving current is reduced in such a manner that, as reflected in the following equation, the temperature sensor monitors an internal temperature of the blood oxygen saturation sensor and when exceeding 42° C., restrict a working pulse width of the LED drive current, simultaneously, $$\mu_{i+1} = \begin{cases} \mu_i - 0.05 & (T_{emp} \geq 42° \text{ C.}) \\ \mu_i & (T_{emp} < 42° \text{ C.}) \end{cases}$$

where $\mu_i$ is a duty ratio of a LED driving current corresponding to a previous temperature measurement period; $\mu_{i+1}$ is a duty ratio of a LED driving current corresponding to a current temperature measurement period; $T_{emp}$ is the internal temperature of the sensor measured in the previous temperature measurement period; and i is a natural number.

Compared with the prior art, the present invention has the following beneficial technical effects.

The electrode according to the present disclosure simultaneously monitors the physiological information about PPG, blood oxygen saturation, temperature and impedance of the blood in the right ventricular cavity. The accuracy of blood oxygen saturation monitoring is improved by cross-comparing the blood oxygen saturation information with the monitored blood temperature information. A rapid response capability of CRAP is improved by monitoring fast-changing right ventricular apical impedance information. The external tissue impedance changes of PPG sensor which indirectly reflect the variation of the tissue thickness. LED driven current is dynamically adjusted by monitoring internal temperature and the external tissue impedance of the PPG sensor. Thereby extending the life time of the PPG sensor.

The method of the present invention provides the cross-comparison of blood oxygen saturation information by monitoring blood temperature information, which is also a slowly changing metabolism, instead of the existing technology that only monitors blood oxygen saturation. In this way, the influence of other physiological processes on blood oxygen saturation measurement can be eliminated, and the accuracy of metabolic evaluation is improved.

The simultaneous monitoring of fast-changing right ventricular apical impedance provides a cross-comparison of blood oxygen saturation and temperature monitoring, instead of the existing technology that only monitors blood oxygen saturation, thereby improving the regulation speed of changes of the metabolism.

Furthermore, instead of the existing technique that allows indulgent growth of the attached biological tissue, the internal temperature of the PPG sensor and the impedance change of the biological tissues attached on the PPG sensor surface are monitored simultaneously to indirectly reflect the thickness change of the attached biological tissues, so as to dynamically adjust the LED driven current and minimize the photothermic stimulation to the growth of connective tissues, thereby prolonging the life time of the PPG sensor.

DESCRIPTION OF EMBODIMENTS

The present invention will be described in details below in conjunction with specific examples, which are explanations and not limitations to the present invention.

The present invention proposes a multi-sensor composite right ventricular electrode and a fused CRAP to address the problems that for example, the existing right ventricular blood oxygen saturation electrode is influenced by many factors for the measurement of blood oxygen saturation, the speed of the CRAP is slow, and the fiber tissues wrapped around the electrode is likely to cause sensor failure.

The concept of the present invention lies in: providing cross-comparison with blood oxygen saturation information by monitoring blood temperature information, which is also a slowly changing metabolism, instead of the existing technology which only monitors blood oxygen saturation, thereby excluding the influence of other physiological processes on the measurement of blood oxygen saturation and improving the evaluation accuracy of the metabolism; providing a cross-comparison of blood oxygen saturation and temperature monitoring by monitoring the fast-changing right ventricular apical impedance at the same time, instead of the existing technology that only monitors the blood oxygen saturation, thereby improving the regulation speed of changes of the metabolism; simultaneously monitoring the internal temperature of the PPG sensor and the impedance change of the attached biological tissues on the surface to indirectly reflect the thickness change of the attached biological tissues, instead of the existing technology that allows indulgent growth of the attached biological tissues, so as to dynamically adjust the LED driving current and minimize the photothermic stimulation to the growth of connective tissues, thereby delaying the failure time of the PPG sensor.

Figure 1:
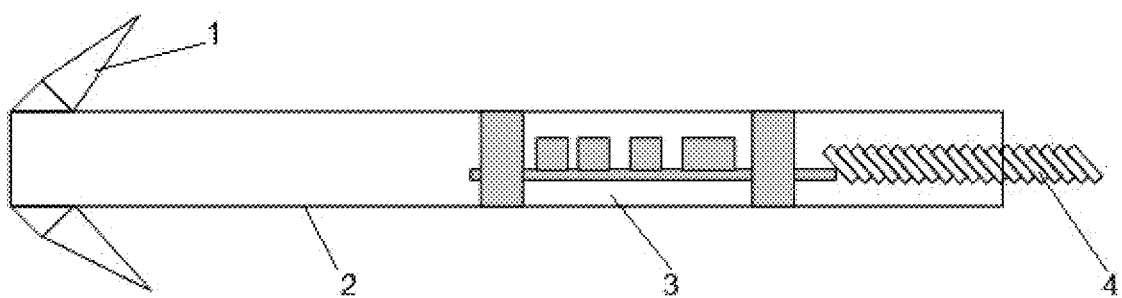
FIG. 1 is a schematic diagram of an electrode structure of the present invention.

Referring to FIG. 1, the multi-sensor composite right ventricular electrode of the present invention includes: a positioning anchor 1, a silicone catheter 2, a sensor compartment 3, and connection wires 4.

The positioning anchor 1 is an anchor-like positioning and fixing device for fixing the electrode at the trabecula muscle of the right ventricular apex and made of biocompatible material silicone.

The silicone catheter 2 is a main body of the electrode, configured to connect the components of the electrode, and made of biocompatible material silicone.

The sensor compartment 3 is configured to install various sensors, including a blood oxygen saturation sensor, a temperature sensor and an impedance sensor. The blood oxygen saturation sensor is composed of one pair of red light and infrared light emitting diodes and one photodiode. The temperature sensor is composed of a thermistor. The impedance sensor is composed of a pair of annular titanium metal electrodes that measure impedance. External materials of the sensor compartment 3 are silicone and metal titanium, both of which are biocompatible materials.

The connection wires 4 are located inside the silicone tube 2 for connecting external connection terminals with excitation and output wires of the sensors.

The venous blood oxygen saturation is detected by a dual-wavelength PPG sensor with 660 nm red light and 940 nm infrared light, which is described by equations (1), (2), and (3):

$$S_pO_2 = \alpha - \beta R \qquad (1)$$

$$S_pO_2 = \alpha - \beta R - \gamma R^2 \qquad (2)$$

$$R = \frac{I_{AC}^{660}/I_{DC}^{660}}{I_{AC}^{940}/I_{DC}^{940}} \qquad (3)$$

where $I_{AC}^{660}$ and $I_{AC}^{940}$ respectively represent alternating-current components of intensities of the red light and infrared light that are reflected by the blood and are measured by the photodiode; and $I_{DC}^{660}$ and $I_{DC}^{940}$ respectively represent direct-current components of the intensities of the red light and infrared light that are reflected by the blood. Therefore, when the direct-current and alternating-current components of the intensities of the red light and infrared light are obtained within a heartbeat interval, the value of R can be calculated, and then the venous oxygen saturation within the heartbeat period can be calculated.

α, β and γ are all empirical values determined by calibration. Equation (1) is a first-order linear relationship between the blood oxygen saturation and R. While the venous blood oxygen saturation does not satisfy the first-order linear relationship, it can be described with a second-order equation (2).

In a preferably embodiment, the 660 nm red LED is SML-LX0603 from LUMEX, the 940 nm infrared LED is SFH4043 from OSRAM, and the photodiode is NJL6401 from JRC.

The temperature is detected with NCP15XH103F03RC thermistor from MURATA, where a relationship between resistance Y of the thermistor and the ambient temperature T is described by equation (4):

$$Y = -kT + b \qquad (4),$$

where k and b are empirical values determined through experiments.

In the detection of impedance, a current source drives a constant current to flow through the biological tissue between a pair of annular titanium metal electrodes, and the potential difference V generated between the annular titanium metal electrodes is detected to provide the impedance information, as described in equation (5):

$$V = CI_m \qquad (5)$$

where C is the constant current generated by the current source, and $I_m$ is the impedance of the biological tissue to be measured.

Figure 2:
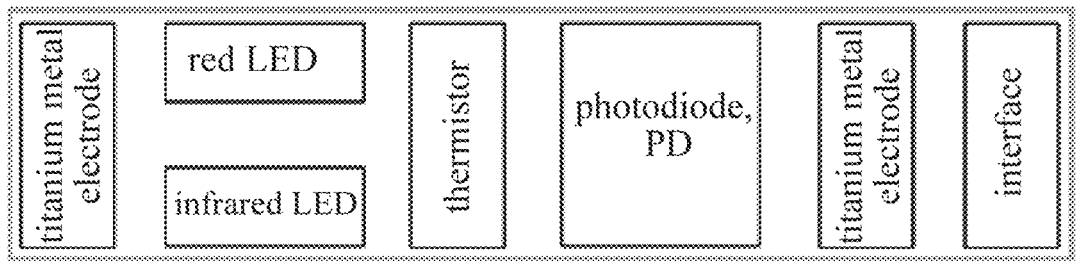
FIG. 2 is the LEDs in parallel position layout for the electrode of the present invention.
Figure 3:
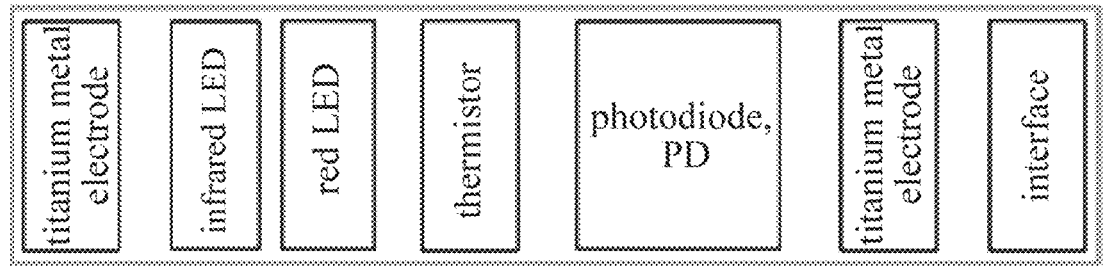
FIG. 3 is the LEDs in series position layout for the electrode of the present invention.

Referring to FIG. 2, in the circuit layout of the sensor compartment 3, the circuit includes, sequentially from a head end to a tail end of the electrode, an impedance measurement positive electrode, two LED light-emitting diodes, a thermistor, a photodiode PD, an impedance measurement negative electrode, and an interface for connecting the wire 4. FIG. 2 shows a circuit element layout in which two LEDs are connected in parallel, and FIG. 3 shows a circuit element layout in which two LEDs are connected in series. Under the preferred conditions of the present invention, the case in which the two LEDs are connected in parallel and the case in which the two LEDs are connected in series have no obvious difference in use.

Figure 4:
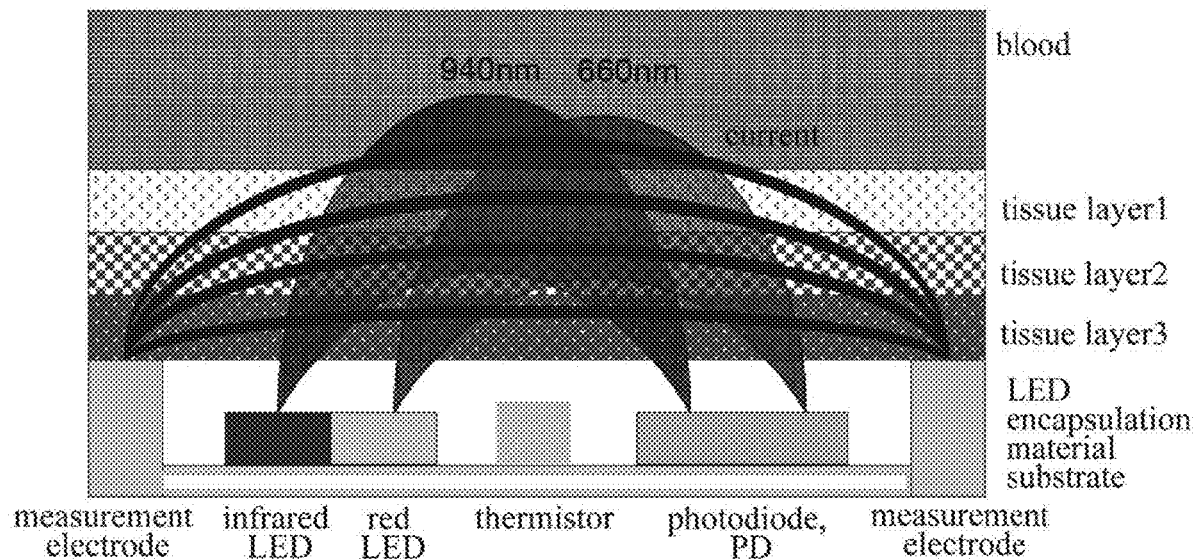
FIG. 4 is a schematic diagram of measurement by the electrodes of the present invention.

FIG. 4 illustrates a schematic diagram of a measurement principle of each sensor in the sensor compartment 3.

In the PPG sensor, a pair of LEDs emit red light and infrared light in a time-division manner, and the red light and infrared light are respectively transmitted through the connective tissue outside the electrode, and then are reflected by the blood to propagate along a banana-shaped route to the photodiode PD. The Reflected PPG signals received by the PD include the blood oxygen saturation information as well as physiological signals of pulse rate, respiration and other components.

The temperature sensor, i.e., the thermistor, first senses a temperature of blood outside the silicone catheter when neither the red LED nor the infrared LED emits light, so as to realize closed-loop control of metabolism-based CRAP of the blood temperature. Secondly, the thermistor can separately sense operating temperatures of the red LED and the infrared LED when both the red LED and the infrared LED emit light in a time division manner, so as to limit the current for emitting the light within an allowable range, thereby preventing excessive growth of the connective tissue attached outside the electrode due to stimulation from the excessively high temperature. Finally, the thermistor disposed between the LEDs and the PD acts as a barrier to prevent the LEDs' light directly entering the photodiode without being reflected by the blood.

The impedance sensor, i.e., the annular titanium metal electrode, when driving with a current, the current passes through the connective tissue attached outside the electrode, and is affected by changes in the impedances of the ventricle and blood volume caused by ventricular pulsation. An impedance-based closed-loop control of the CRAP can be obtained from the alternating-current component of the impedance signal fluctuation; and the thickness information of the connective tissue attached outside the electrode can be obtained from a direct-current component, thereby monitoring the growth status of the connective tissue, dynamically adjusting the intensity of light emitted by the LEDs, and avoiding excessive growth of connective tissue stimulated by high intensity light.

Figure 5:
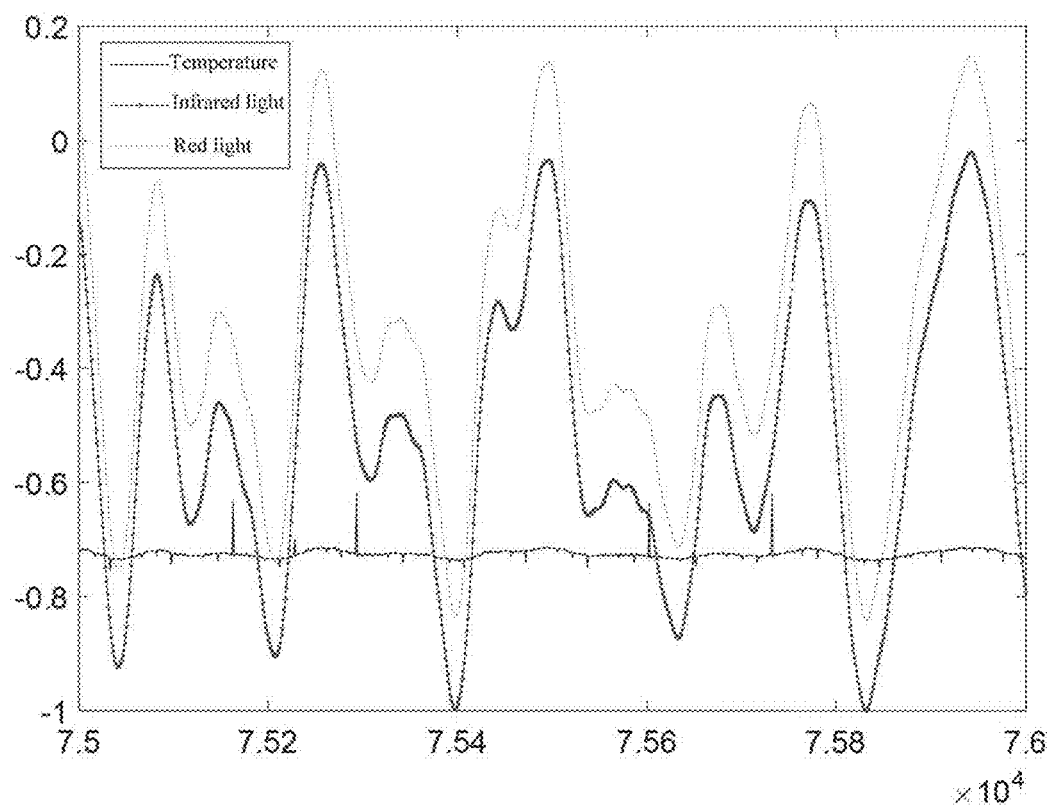
FIG. 5 is a diagram of physiological signals measured by the electrode of the present invention from a beagle's right ventricle.

FIG. 5 is a diagram of physiological signals measured by the electrode of the present invention from a beagle's right ventricle according to the present invention. In the figure, a dual-wavelength PPG waveform per heartbeat and a synchronizing blood temperature waveform can be clearly observed.

Figure 6:
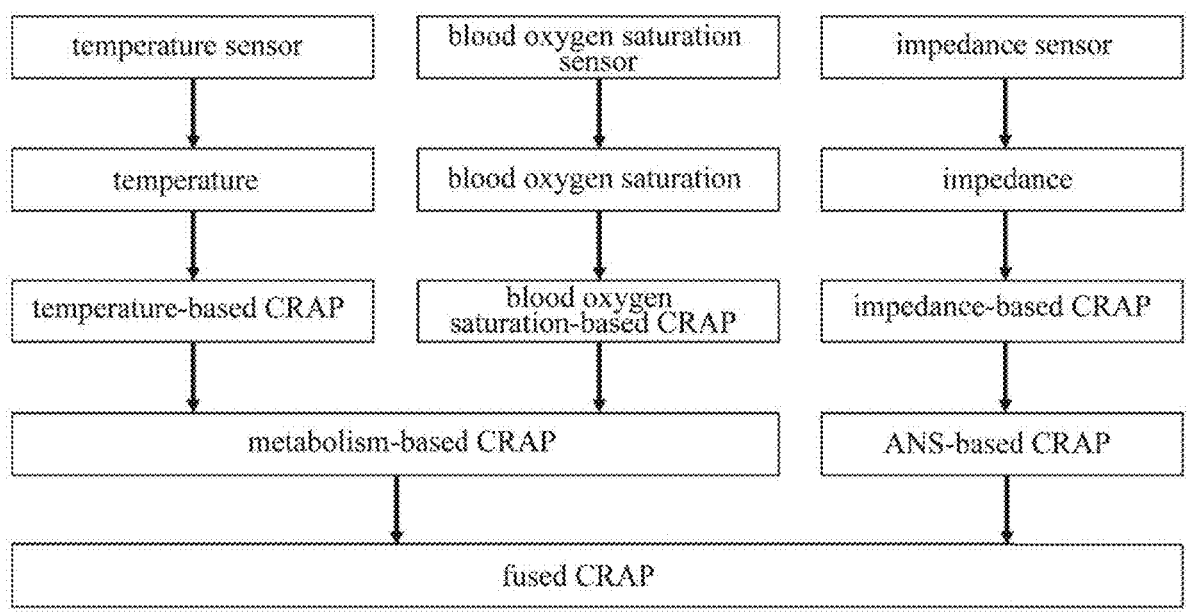
FIG. 6 a flowchart of a fused CRAP.

As shown in the flowchart of a fused CRAP in FIG. 6, the right ventricular blood temperature, the blood oxygen saturation, and the right ventricular apical impedance information are obtained with the temperature sensor, the PPG sensor, and the impedance sensor of the right ventricular electrode, respectively. The correspondingly adjusted heart rates are generated on basis of the heart right ventricular blood temperature-based CRAP, the right ventricular blood oxygen saturation-based CRAP and the right ventricular apical impedance-based CRAP respectively. The metabolism-based CRAP is generated through a cross-comparison between the right ventricular blood temperature-based CRAP and the right ventricular blood oxygen saturation-based CRAP. The autonomic nervous system (ANS)-based CRAP is generated through the right ventricular apical impedance-based CRAP. Ultimately, the fused CRAP is generated through a cross-comparison between the metabolism-based CRAP and the ANS-based CRAP.

Replacing a simply right ventricular blood oxygen-based CRAP, the cross-comparison with the right ventricular blood oxygen saturation-based CRAP is provided by monitoring the right ventricular blood temperature-based CRAP, which is also a slowly changing metabolism, thereby eliminating the influence of other physiological processes on the measurement of the blood oxygen saturation, and improving the accuracy of the evaluation of the metabolism, as shown in equation (6):

$$P_{Meta} = \begin{cases} k_1 P_{Temp} + k_2 P_{S_pO_2} & (P_{Temp} \leq P_{S_pO_2}) \\ P_{Temp} & (P_{Temp} > P_{S_pO_2}) \end{cases} \quad (6)$$

where $P_{Meta}$ represents the metabolism-based CRAP through the cross-comparison; $P_{Temp}$ represents the right ventricular blood temperature-based CRAP; $P_{S_pO_2}$ represents the right ventricular blood oxygen saturation-based CRAP; and $k_1$ and $k_2$ are weight coefficients obtained through experiments, preferably $k_1=k_2=0.5$.

Replacing a simply right ventricular blood oxygen saturation-based CRAP, a cross-comparison with the right ventricular blood temperature-based CRAP and blood oxygen saturation-based CRAP simultaneously and monitoring the fast-changing right ventricular apical impedance-based CRAP, thereby optimizing the adjusting speed of the metabolism as shown in equation (7):

$$P_{Blend} = \begin{cases} k_3 P_{Meta} + k_4 P_{Imp} & (P_{Meta} \leq P_{Imp}) \\ P_{Meta} & (P_{Meta} > P_{Imp}) \end{cases} \quad (7)$$

where $P_{Blend}$ represents the fused CRAP obtained through the cross-comparison; $P_{Imp}$ represents the right ventricular apical impedance-based CRAP; and $k_3$ and $k_4$ are weight coefficients obtained through experiments, preferably, $k_3=k_4=0.5$.

Figure 7:
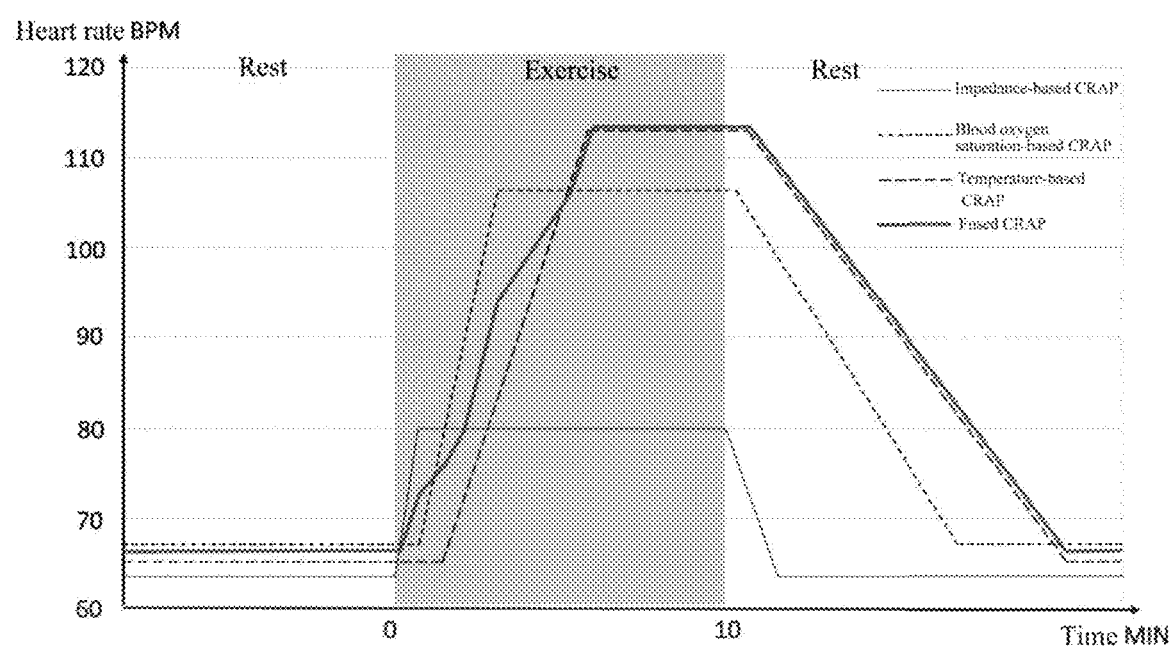
FIG. 7 is a diagram illustrating the relationship between exercise and the heart rate of the fused CRAP.

FIG. 7 is a diagram illustrating the relationship between exercise and the heart rate of the fused CRAP. Under the rest-exercise-rest conditions, the right ventricular blood temperature-based CRAP, the right ventricular blood oxygen saturation-based CRAP and the right ventricular apical impedance-based CRAP generate the corresponding heart rate curves respectively, and the fused CRAP is obtained ultimately through cross-comparison.

Figure 8:
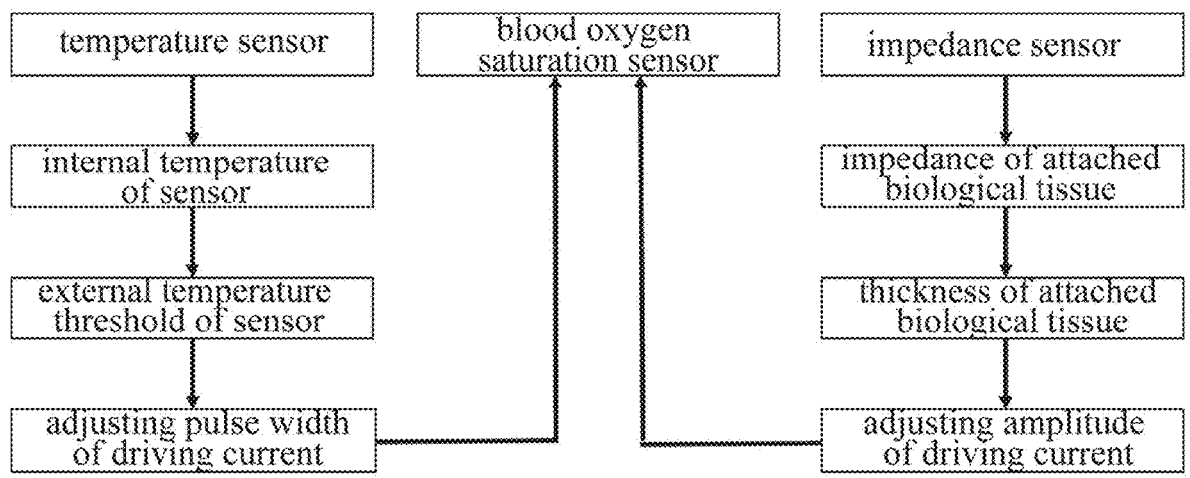
FIG. 8 is a flowchart of the driving current adjustment steps of the PPG sensor; and In the drawings: positioning anchor 1, silicone catheter 2, sensor compartment 3, and connecting wire 4.

FIG. 8 is a flowchart of the driving current adjustment steps of the PPG sensor. The internal temperature of the sensors and the impedance of the biological tissues attached to the external surfaces of the sensors can be acquired through the temperature sensor and the impedance sensor of the composite right ventricular electrode, respectively. The pulse width of the LED driving current in the PPG sensor is dynamically adjusted by comparing with a threshold value of the external temperature of the sensor. The amplitude of the LED driving current in the PPG sensor is dynamically adjusted by acquired the thickness information of the biological tissue attached to the external surface of the sensor is through the impedance change of the attached biological tissue, therefore to minimize the attachment of biological tissue on the sensor surface and extend the service life of the sensor.

The thickness change of the attached biological tissue is indirectly reflected by the monitored change of the impedance of the attached biological tissue on the surface of the PPG sensor, so as to dynamically adjust the LED driving current, as shown in equation (8):

$$\Delta I_m = k_5 \left(1 - \left(\frac{R_0}{R_0 + \Delta H}\right)^2\right); \text{ or} \quad (8)$$

$$\Delta H = R_0 \left(\sqrt{\frac{k_5}{k_5 - \Delta I_m}} - 1\right) \quad (9)$$

$\Delta I_m$ represents the monitored change of impedance of a biological tissue attached to a surface of a PPG sensor; $R_0$ represents a radius of an outer surface of the PPG sensor; $\Delta H$ represents the change of the thickness of the biological tissue attached to the surface of the blood oxygen saturation sensor; $k_5$ is a proportional coefficient related to a resistivity of the biological tissue, the radius of the outer surface of the PPG sensor, and a distance between measuring electrodes and is obtained through experiments. The impedance changes of the attached biological tissue between the electrodes on the sensor surface from equation (9), and in turn a change amount of the thickness of the attached biological tissue can be obtained.

According to Lambert's law, the red light and infrared light emitted by the LED in the PPG sensor driven by a constant driving current are affected by the slowly increasing thickness of the biological tissue attached to the sensor surface, and the intensity of the emitted light will slowly decrease, as shown in equation (10). Therefore, the signal-to-noise ratio of the PPG sensor is gradually reduced, which affects the quality of the detected signal.

$$I = I_0 e^{-k_6 \Delta H} \quad (10)$$

I is an intensity of light transmitted through the biological tissue, $I_0$ is an emission intensity of the LED, $k_6$ is a product of a light absorption coefficient of the biological tissue and a concentration of a light absorption substance and is a constant when the concentration is stable. $\Delta H$ is the change amount of the thickness of the biological tissue attached to the surface of the PPG sensor. In order to prevent the intensity I of light of the LED transmitted through the biological tissue from being affected by the slowly increasing thickness of the attached biological tissue on the surface, the emission intensity $I_0$ should be increased by $e^{k_6 \Delta H}$ times when the thickness of the attached biological tissue is increased by $\Delta H$, as shown in equation (11):

$$I_0 = I e^{k_6 \Delta H} \quad (11)$$

In the case where the driving current is smaller than a saturation driving current, the emission intensity of the LED is substantially proportional to the driving current, and thus the adjustment of the emission intensity of the LED can be achieved by changing the driving current. That is, when the thickness of the attached biological tissue is increased by $\Delta H$, the driving current $C_{D0}$ should be increased by $e^{k_6\Delta H}$ times, as shown in equation (12):

$$C_{D0}=C_D e^{k_6\Delta H} \qquad (12)$$

$C_D$ is the driving current when generating the intensity I of light transmitted through the biological tissue, and $C_{D0}$ is a driving current when generating an emission intensity $I_0$ of an LED. The working pulse width of the LED driving current not only affects an average value of the LED driving current, also directly affects heat generation of the LED. Under the constant driving current $C_D$, the pulse width of the working pulse with a period $T_{period}$ and a duty ratio $\mu$ is $\mu T_{period}$, the average driving current is $\mu C_D$, and $\mu$ generally ranges from 0.25 to 0.50, and is preferably 0.50. The LED emits light during the working pulse width $\mu T_{period}$ generates heat, and causes internal temperature rise of the sensor while dissipating heat by external blood flow to reduce the internal temperature of the sensor. During the remaining period $(1-\mu)T_{period}$, it does not emit light, does not generate heat, and only dissipates heat by external blood flow to reduce the internal temperature of the sensor.

As the internal temperature of the sensor increases or the driving current increases, both the thermal resistance and the junction temperature of the LED gradually increase. The light efficiency gradually decreases, reducing the service life of the LED and thus increasing the external surface temperature of the sensor. When the external surface temperature exceeds 42° C., it will cause denaturation of proteins in the surrounding blood, directly stimulating the rapid growth of the connective tissue attached to the surface of the PPG sensor. Therefore, the temperature sensor is configured to monitor the internal temperature of the PPG sensor at the same time, and the working pulse width of the LED driving current will be limited when it exceeds 42° C. As shown in equation (13):

$$\mu_{i+1} = \begin{cases} \mu_i - 0.05 \ (T_{emp} \geq 42° \text{ C.}) \\ \mu_i \ (T_{emp} < 42° \text{ C.}) \end{cases} \qquad (13)$$

$\mu_i$ is a duty ratio of a LED driving current corresponding to a previous temperature measurement period; $\mu_{i+1}$ is a duty ratio of a LED driving current corresponding to a current temperature measurement period; $T_{emp}$ is the internal temperature of the sensor measured in the previous temperature measurement period; and i is a natural number. The internal temperature of the sensor is measured every minute. When the internal temperature exceeds 42° C., the duty ratio $\mu$ is decreased by 0.05. Each time when the duty ratio $\mu$ is adjusted, the average driving current is decreased by $0.05C_D$, and the working pulse width is decreased by $0.05T_{period}$. In the worst case, the adjustment is performed continuously 5 times within 5 minutes to reduce the average driving current by a half and reduce the working pulse width by a half, in order to reduce the internal temperature of the sensor by heat dissipation depending on external blood flow, and in turn reduce the surface temperature of the sensor and slow down the growth of the connective tissue attached to the surface. The system restores the duty ratio $\mu$ to 0.05 every one hour to maintain the normal driving current of the LED.

In view of the above, the LED driving current is dynamically adjusted by monitoring the change of the impedance of the biological tissue attached to the surface of the PPG sensor, which indirectly reflects the change of the thickness of the attached biological tissue. Replacing the existing technology with a large driving current and a wide working pulse width to excessively stimulate the growth of attached biological tissue, the present invention provides a method using two simultaneous measures, monitoring the internal temperature of the photoelectric volumetric wave sensor while limiting the working pulse width of the LED with the temperature sensor. In this way, the excessively high driving current and wide working pulse width are prevented from causing excessive light and heat, which may excessively stimulate the connective tissue growth, thereby delaying the failure time of the PPG sensor as longer as possible.

What is claimed is:
1. A multi-sensor composite right ventricular electrode, comprising:
   a silicone catheter (2);
   a positioning anchor (1) disposed outside one end of the silicone catheter (2);
   a sensor compartment (3) disposed in the silicone catheter (2); and
   a connecting wire (4) connected to the sensor compartment (3),
   wherein the sensor compartment (3) comprises a printed circuit board (PCB), as well as a blood oxygen saturation sensor, a temperature sensor and an impedance sensor that are provided on the PCB, and
   wherein the PCB is connected to one end of the connecting wire (4) via an interface,
   wherein the blood oxygen saturation sensor is a dual-wavelength photoplethysmography (PPG) sensor comprising a red LED configured to emit red light, an infrared LED configured to emit infrared light and a photodiode configured to detect reflected red light and/or infrared light, wherein the red LED, the infrared LED and the photodiode are located on a PCB;
   wherein the temperature sensor is composed of a thermistor provided on the PCB;
   wherein the impedance sensor comprises a pair of titanium metal electrodes arranged on the PCB and configured to form an impedance measurement loop with a biological tissue to be measured, and the titanium metal electrodes are ring-shaped and are embedded on the silicone catheter (2); and
   wherein the thermistor is configured to: sense a temperature of blood outside the silicone catheter (2) when neither the red LED nor the infrared LED emits light sense operating temperatures of the red LED and the infrared LED when both the red LED and the infrared LED emit light in a time division manner; and prevent the light emitted from LEDs entering the photodiode directly without being reflected by the blood.

2. The multi-sensor composite right ventricular electrode according to claim 1, wherein the red LED and the infrared LED are connected in parallel or in series to form a unit, and the unit, the thermistor and the photodiode are sequentially arranged between the pair of titanium metal electrodes.

3. The multi-sensor composite right ventricular electrode according to claim 1, wherein venous blood oxygen saturation is detected by a dual-wavelength PPG sensor with 660 nm red light and 940 nm infrared light, and is described with an equation (1) or (2):

$$S_pO_2=\alpha-\beta R \qquad (1)$$

$$S_pO_2=\alpha-\beta R-\gamma R^2 \qquad (2)$$

where $I_{AC}^{660}$ and $I_{AC}^{940}$ respectively represent alternating-current components of intensities of the red light and infrared light that are reflected by the blood and are measured by the photodiode; $I_{AC}^{660}$ and $I_{AC}^{940}$ respectively represent direct-current components of the intensities of the red light and infrared light that are reflected by the blood;

$$R = \frac{I_{AC}^{660}/I_{DC}^{660}}{I_{AC}^{940}/I_{DC}^{940}};$$

and α, β and γ are all empirical values determined by calibration; and the equation (1) is a first-order linear relationship between the blood oxygen saturation and R. While the venous blood oxygen saturation does not satisfying the first-order linear relationship, it can be described with a second-order equation (2).

\* \* \* \* \*